(12) United States Patent
Reay-Young

(10) Patent No.: US 6,478,753 B2
(45) Date of Patent: Nov. 12, 2002

(54) TENSION MEASURING DEVICE

(75) Inventor: Clive Reay-Young, N. Yorkshire (GB)

(73) Assignee: Atlantech House, N. Yorkshire (GB)

( * ) Notice: Subject to any disclaimer, the term of this patent is extended or adjusted under 35 U.S.C. 154(b) by 3 days.

(21) Appl. No.: 09/862,580

(22) Filed: May 23, 2001

(65) Prior Publication Data

US 2001/0049483 A1 Dec. 6, 2001

(30) Foreign Application Priority Data

May 31, 2000 (GB) .............................................. 0013037

(51) Int. Cl.$^7$ .............................................. A61B 5/103
(52) U.S. Cl. .......................... 600/595; 600/587; 73/789
(58) Field of Search .............................. 600/587, 595; 606/96; 73/789

(56) References Cited

U.S. PATENT DOCUMENTS

| | | | | |
|---|---|---|---|---|
| 3,905,356 A | * | 9/1975 | Fletcher et al. | 600/587 |
| 4,204,544 A | * | 5/1980 | Feldstein et al. | 600/595 |
| 4,583,554 A | * | 4/1986 | Mittelman et al. | 600/587 |
| 4,712,542 A | * | 12/1987 | Daniel et al. | 606/96 |
| 4,969,471 A | * | 11/1990 | Daniel et al. | 600/587 |
| 5,037,426 A | * | 8/1991 | Goble et al. | 606/96 |
| 5,911,695 A | * | 6/1999 | Watkins et al. | 600/587 |

FOREIGN PATENT DOCUMENTS

| | | |
|---|---|---|
| EP | 0 379 789 | 8/1990 |
| WO | 96/39934 | 12/1996 |
| WO | 98/38937 | 9/1998 |

* cited by examiner

Primary Examiner—Steven J. Ganey
(74) Attorney, Agent, or Firm—Nixon & Vanderhye

(57) ABSTRACT

The invention describes a device used to measure the tension of a soft tissue 24 attached to bones 20,22. The device 2 comprises a body region 4 having force applying hook shaft 6a and abutment spike shaft 8a extending outwardly therefrom. A spike region 8b of the abutment spike shaft 8a is extended in direction X to thereby abut the surface of bone 22. The force of the abutment is measurable by a displacement on a translation scale 14. An operator pulls on the device 2 in direction Y thereby applying an anterior force (measured by a displacement on a force scale 14) to the tissue 24 via a hook region 6b of the force applying hook shaft 6a. The application of said anterior force on to the tissue 24 results in an anterior translation of the tissue 24. The tension of the tissue 24 may be calculated from the displacements on the force scale 12 and translation scale 14.

20 Claims, 2 Drawing Sheets

TENSION MEASURING DEVICE

The present invention relates to a tension measuring device, and particularly, but not exclusively, relates to a tension measuring device for graft fixation, for example, tendon or ligament fixation.

Due to increasing involvement of people with active sport, injuries are becoming increasingly common where tissues such as ligaments or tendons tear or detach from bone. Surgical techniques have been developed to reconstruct such soft tissues and to re-attach them to the relevant bone. Some of the most common types of such injuries are tearing of the anterior or posterior cruciate ligament (ACL or PCL). Reconstruction of such tissues generally involves replacement with a graft such as autologous or artificial tendon. An autologous tendon graft may be taken from the patients patella tendon or, alternatively, the Semi-tendinosus or Semitendinosus/Gracilis may be utilised.

A particularly important issue in these and other grafting operations is that the graft is fixed in the bone tunnel at the required and at a reproducible tension.

Therefore, in an attempt to improve the quality and consistency of arthroscopic ACL or PCL replacement, surgeons are paying more attention to the level of pre-tensioning applied to the graft prior to it being locked in place. The ultimate goal is to place the graft into the knee joint and lock it at a tension which accurately replicates the normal cruciate ligament of the patient. U.S. Pat. No. 5,713,897 describes an ACL tensioning device which maintains a required tensile stress on the distal end of a cruciate ligament graft fixed in the femoral tunnel section, and for maintaining that applied tensile stress as the ligament is mounted in or onto the tibia. However, this and other current methods of tensioning the distal end of the graft below the tibial tunnel are somewhat without justification as there is no way of measuring the tension of a normal ACL at its distal point. An applied force at this point could be said to be irrelevant, as there is no standard to compare against.

With a view to addressing the problems of the prior art mentioned above, or otherwise, it is one of the aims of at least preferred embodiments of the present invention to provide a device which, instead of applying a known tension to the distal end of the graft, measures the resultant effect that the tension applied at this point has on the graft in the joint.

According to a first aspect of the present invention, there is provided a tension measuring device suitable for measuring the tension of soft tissue attached to bone, the device comprising a body region, force applying means extending from said body and operable to apply a translational force to soft tissue attached to bone, and abutment means extending from said body and operable to abut, in use, a bone to which the soft tissue is attached, the abutment means being responsive to the application of translational movement to the force applying means to thereby measure the applied translational movement and the force applying means being responsive to the tension in the soft tissue to transfer said applied translational movement to the soft tissue below a predetermined soft-tissue tension and to extend above the said predetermined tension to prevent further translation of the soft tissue.

Preferably, the extension of the force applying means is measured by suitable measuring means such as an associated translation scale.

Preferably, the force applying means is resiliently longitudinally deformable. Preferably, the abutment means is resiliently longitudinally deformable. Preferably, the abutment means distal end is biased, preferably, longitudinally biased, towards the bone, in use, to remain in contact therewith during the application of translational movement away from the bone. Preferably, the force applying means is under a fixed tension with respect to elongation thereof. Preferably, the fixed tension is applied by means of a tension spring which engages the force applying means to prevent elongation below a pre-determined applied force.

Preferably, the device measures the tension in the soft tissue by determining the extent of the translational movement of the soft tissue in response to the force applying means.

Advantageously, instead of applying a known force to the distal end of the soft tissue, the device measures the effect the applied force has on the soft tissue and thereby the tension in the soft tissue. Preferably, the device is used to measure the tension of the soft tissue which is attached to the bone by both the proximal and distal ends of said soft tissue.

Preferably, the force applying means and the abutment means extend outwardly in the same direction from the body region. Preferably, the force applying means and the abutment means are, preferably, spaced from each other and, preferably, substantially parallel to one another.

Preferably, the abutment means is operable to abut the anterior surface of a tibia bone, more preferably, the proximal anterior surface of the said bone. Preferably, the abutment means comprises an elongate shaft with, preferably, spike means at the distal end thereof, the spike means being operable to make a firm contact with the bone. Preferably, the abutment means comprises resilient means which urges the elongate shaft into abutment with the bone. The resilient means may be a compression spring which engages a proximal part of the abutment means to urge it into abutting contact with the bone.

The abutment means may further comprise locking means to lock the abutment means in a retracted position. The locking means may be released thereby urging the abutment means outwards towards the bone. Preferably, the abutment means comprises suitable translation measuring means, preferably, a translation scale on which the applied translational movement, typically, translation of the body region with respect to the bone may be measured. The translation scale may be located within the body region at the proximal end of the abutment means to that of the bone abutting end.

The translation scale may be analogue or digital.

Preferably, the force applying means is a pulling means which is placed, preferably, in direct contact with the soft tissue to which the translation force is to be applied. Preferably, the pulling means is adapted at its distal end to abut at least part of the rearwardly facing side of the soft tissue with respect to the body of the device. Preferably, the pulling means comprises a hooking means which is hookable around the soft tissue. Preferably, the pulling means comprises an elongate shaft which has hooking means at the distal end thereof. Preferably, the hooking means is hooked around the rear of the soft tissue and arranged to apply translational force to the soft tissue in the required direction.

Preferably, the pulling means comprises resilient means which is arranged to apply a pre-determined force to the soft tissue resulting from the translational movement applied to the tissue by the user. The resilient means may be associated with the pulling means and may be a spring, preferably a tension spring which, preferably, engages at least part of the pulling means.

Preferably, the force applying means is associated with a translation scale by which the elongation of the force applying means and thereby the tissue may be measured. The translational movement in the tissue is determined by subtracting the elongation of the force applying means from the applied translational movement. The translation scale may be located within the body region of the device. The translation scale may be analogue or digital and may measure the extent of the movement of the soft tissue under a specific force of the resilient means and this may be measured in appropriate units. Preferably, a tension spring at a pre-determined tension is used in engagement with the force applying means.

The pulling means may comprise adjustment means to adjust the resilience or pre-determined tension of the pulling means.

The device may be used to measure the tension of any soft tissue attached to any bone. Preferably, the device is used for measuring the tension of a ligament in a joint where a known tension needs to be applied to the ligament. Most preferably, the device is used to measure the tension of anterior cruciate ligaments (ACL). The device may be used to measure the tension of an ACL in a healthy individual. Alternatively, or additionally, the device may be used to reproduce this reference tension in a reconstructed graft such as an ACL.

According to a second aspect of the present invention, there is provided a method of measuring the tension of soft tissue attached to at least one bone comprising applying a translational movement under a pre-determined force to the tissue using a force applying means on a device according to the first aspect of the invention to thereby cause a measurable translational movement of the tissue with respect to the said at least one bone.

The method may comprise one or more of the steps of:
(i) introducing the force applying means to the soft tissue;
(ii) urging the abutment means against at least one bone in contact with the said soft tissue; and
(iii) applying the force to the soft tissue such that the translational movement is in the direction required.

Preferably, the translational movement applied and the elongation of the force applying means is measured and, it is from these that the tension of the soft tissue is determined. Preferably, the translational movement of the soft tissue is measured by subtracting the elongation of the force applying means from the translational movement applied.

The force applying means may be introduced to the soft tissue through an aperture in a patient being treated. Preferably, the aperture is an arthroscopic portal. Preferably, the force applying means comprises an elongate shaft and hooking means at the distal end thereof. Preferably, the hooking means is hooked around the rear of the soft tissue and is arranged to apply translational force to the soft tissue in the required direction.

The method of the second aspect may utilise any one or any combination of features of the first aspect or the preferred features of the first aspect.

The locking means may be operable to lock the abutment means in at least one position. The abutment means may be pulled proximally in a first direction and the locking means is operable to lock the now retracted abutment means at a first position. The locking means may be released to allow the abutment means to be urged distally from the first retracted position to an un-retracted, second position under the resilient force of the compression spring. The position of the abutment means, when in a retracted position, may be variable and determined by the operator.

The method may further comprise the step of:
(i) releasing the locking means such that the abutment means is urged against the tibia.

Preferably, the translation force is applied to the soft tissue via the force applying means by moving the body of the device away from the soft tissue whilst the abutment means remains in contact with the bone. Preferably, the force applied by the force applying means is pre-determined. Preferably, the force applying means comprises a scale from which the translation of the force applying means may be measured. Preferably, the abutment means and force applying means comprise scales from which the translation of the soft tissue may be calculated. Preferably, the degree of translation of the soft tissue is determined by reading off a measurement on the abutment translation scale and subtracting the measurement read off the force translation scale. Preferably, the abutment translation scale moves in response to a compression spring as the body of the device is moved away from the bone and, preferably, the force applied translation scale is moved in response to elongation of the force applying means in response to the tension in the soft tissue.

The method may be used to measure the tension of any soft tissue attached to any bone. Preferably, the method is used for measuring the tension of a ligament in a joint where a known tension needs to be applied to the ligament. Most preferably, the method is used to measure the tension of anterior cruciate ligaments (ACL). The method may be used to determine the tension of an ACL in a healthy individual. Preferably, routine arthroscopies are carried out in order to obtain an average value of the tension in the ACL of healthy individuals. Alternatively, or additionally, the method may be used to reproduce this reference tension in a reconstructed graft ACL. Once an average value of the tension of normal healthy ACLs has been obtained, a surgeon may then aim to reproduce this by tensioning the distal end of a graft ACL and measuring the translation of this ACL. Preferably, this is repeated until the reference translation is achieved in the joint, at which time the ACL may be locked in place either immediately or, preferably, following cycling of the joint and re-checking the tension in case any stretch of tissues or proximal fixation slippage has occurred. It is not necessary to apply excessive force to the normal or graft ACL to achieve accurate results since applying the same force time after time is the key to reproducibility.

It should be further noted that although the above example refers to ACL fixation, this invention is not limited to this application and it will be clear to the skilled technician that the device has numerous applications in connection with the replacement of any ligaments in the human or animal body.

All of the features disclosed herein may be combined with any of the above aspects in any combination.

An embodiment of the invention will now be described by way of example, with reference to the accompanying diagrammatic drawings, in which.

Figures 1A, 1B:
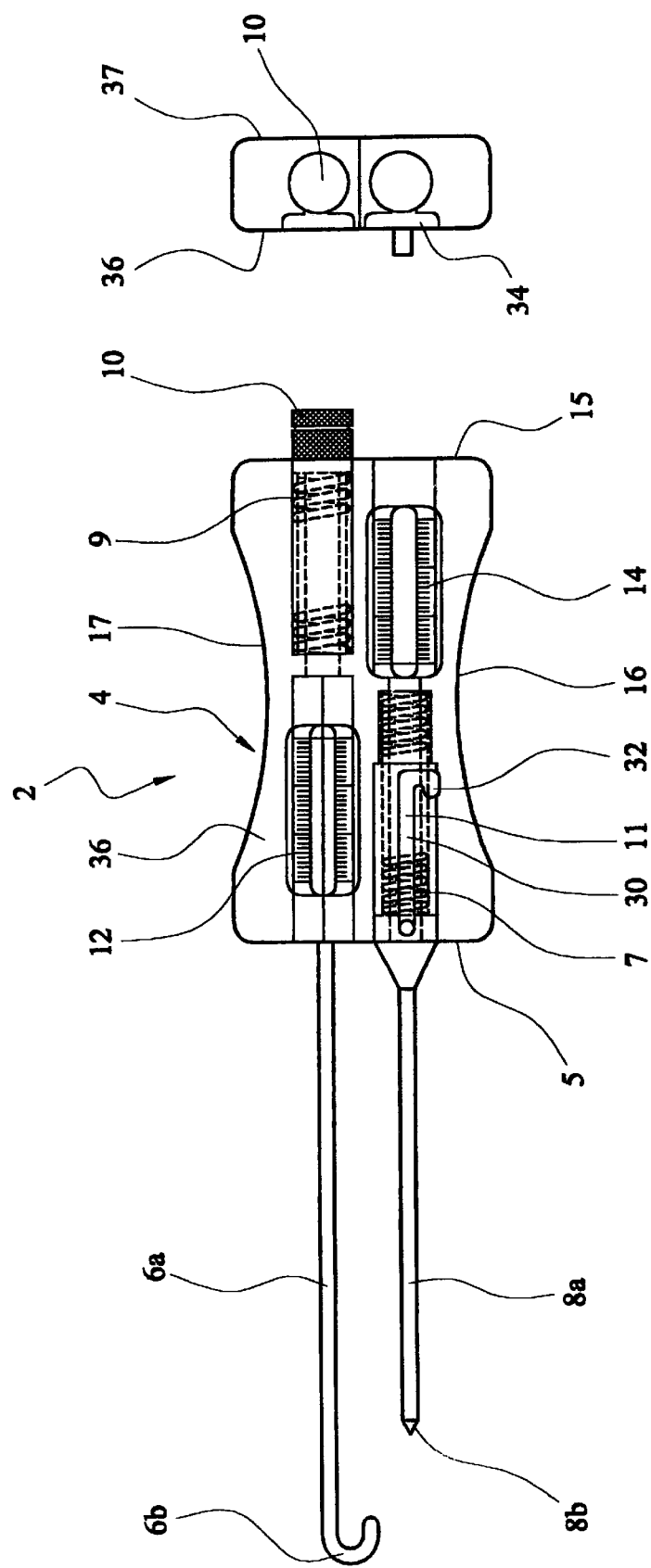
FIG. 1a is a schematic plan view of a tension measuring device in accordance with the invention.
FIG. 1b is a schematic end on view of the tension measuring device.

Referring to FIGS. 1a and 1b, a tension measuring device 2 comprises a rectangular box-shaped body region 4 having flat, distal and proximal end faces 5, 15 which are parallel with each other, two opposing side faces 16,17 extending between the said two end faces 5, 15 and upper and lower parallel faces 36,37, respectively.

The central portion of each opposing side face 16,17 is concavely arcuate to ease the gripping thereof by the hand of a user. Extending outwardly from and through the distal end face 5 of the body region 4, there are two spaced, substantially parallel elongate shafts 6a and 8a. A hook 6b is formed at the distal end of the longitudinally extendable shaft 6a and a spike 8b is formed at the end of the longitudinally extendable shaft 8a. The proximal end of the hook shaft 6a extends longitudinally through the end face 5 and into the body 4 terminating at an adjustment means 10 which is located at, and abuts the outer surface of the proximal end face 15. The adjustment means 10 is present to alter the tension of the hook shaft 6a, the outer surface of the adjustment means 10 being knurled to improve gripping by the user.

A tension spring 9 surrounds and engages a portion of the proximal end of the hook shaft 6a inside the body region 4. A force scale 12 is present extending adjacently along a portion of the longitudinal axis of the hook shaft 6a distal to the tension spring 9 on which the elongation of the hook shaft 6a at the pre-determined tension can be read off and measured. The force scale 12 is graduated into mm and cm divisions but it will be appreciated that any method of display, such as digital LED's, may be used.

The proximal end of the spike shaft 8a extends longitudinally into the end face 5 and through the body region 4. A translation scale 14 is present extending along a portion of the longitudinal axis of the proximal end of the spike shaft 8a. The applied translational movement can be read off the translation scale 14 and measured thereon. A compression spring 7 surrounds and engages a portion of the spike shaft 8a inside the body region 4 distal to the translation scale 14. The compression spring urges the abutment means to elongate towards the bone.

A locking means 11 is attached to the spike shaft 8a and is operable to lock the spike shaft 8a in a retracted position prior to use. The locking means 11 comprises an elongate portion 30, the majority of which is attached to the spike shaft 8a, and the free end of which forms a hook 32. An elongate slot 34 is present in the upper surface 36 of the body region 4 and extends along a longitudinal portion of the body region 4 in a direction which is parallel with axis of the spike shaft 8a. The proximal end of the slot 34 bends so that it extends in a direction which is perpendicular to the axis of the spike shaft 8a. The spike shaft 8a is arranged into a retracted position by pulling back on the locking means 11 in a direction which is parallel with the axis of the spike shaft 8a. The locking means 11 moves rearwardly within the slot 34. The spike shaft 8a is maintained in the retracted position by pushing the hook 32 of the locking means 11 in a direction which is perpendicular to the axis of the body region 4 such that the hook abuts the portion of the slot which is perpendicular to the spike shaft 8a. The locking means and, hence, spike shaft 8a, are maintained in the retracted position under the resilient action of the compression spring 7.

Figure 2:
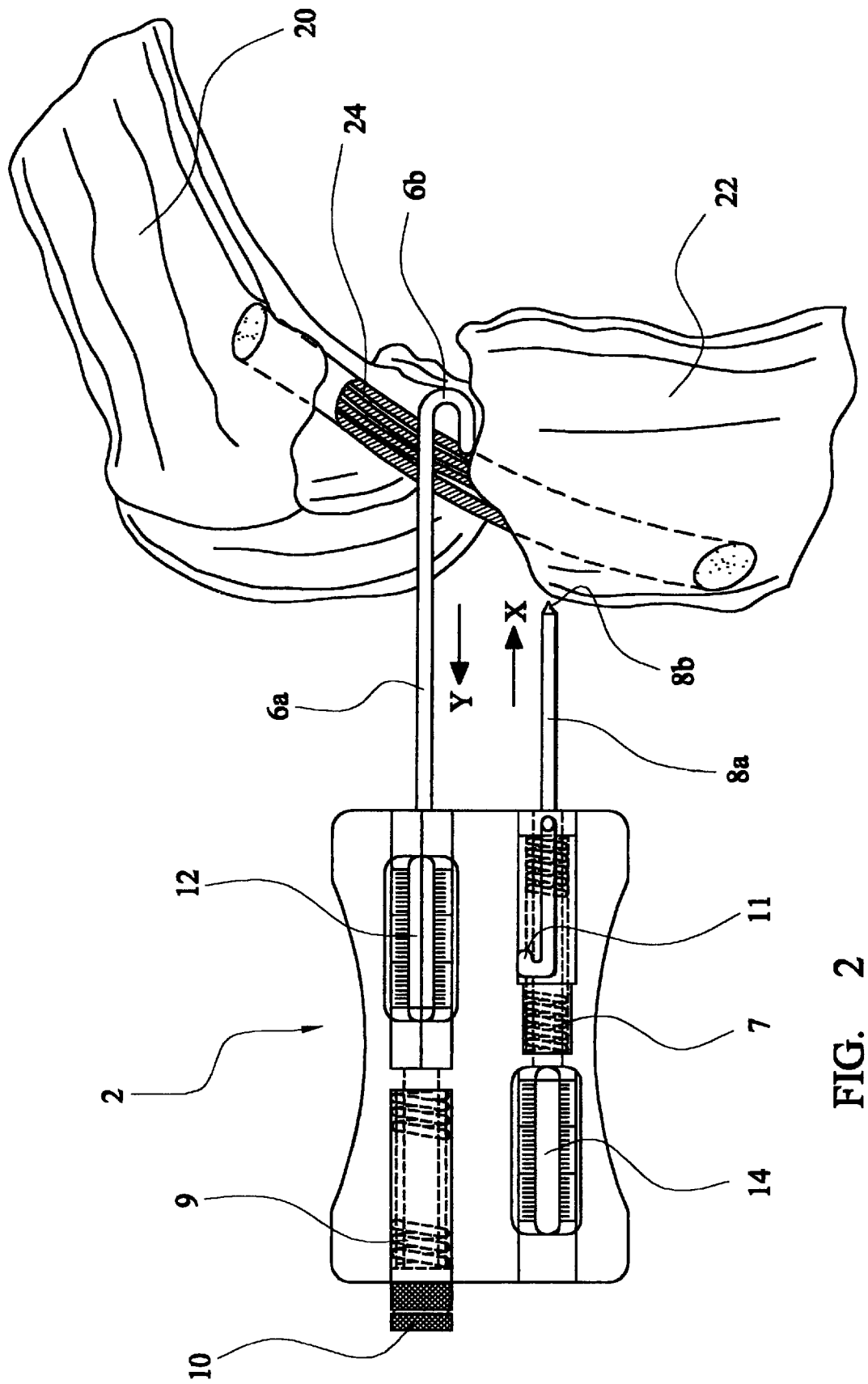
FIG. 2 shows the tension measuring device in use during a graft reconstruction of an ACL.

Referring to FIG. 2, the tension measuring device 2 is shown in use in conjunction with an anterior cruciate ligament (ACL) 24. The device can either be used to determine the tension of a normal ACL 24 in a healthy individual, or be used to reproduce this reference tension in a reconstructed graft ACL 24.

An operator (not shown) holds the body region 4 of the device 2 and first introduces the hook region 6b of the hook shaft 6a through an arthroscopic portal (not shown) in a patient. The hook region 6b is positioned such that it hooks substantially behind and closely abuts the ACL 24 under examination. The spike region 8b of the spike means 8a, which is initially locked in a retracted position by the locking means 11, is then released and extended so that it abuts the proximal anterior surface of the tibia 22.

The operator then pulls on the device 2 in a rearward direction as indicated by arrow Y thereby applying a "draw force" or "anterior load", for example, the equivalent of 101b, to the ACL 24. The application of this anterior load onto the ACL 24 results in an anterior translation of the ACL 24 in the same direction as indicated by arrow Y until the tension in the ACL is equal to that of the hook shaft. Thereafter, the hook shaft elongates under the tension of the ligament and the movement may be measured on the associated translation scale. The length of said translation is calculated from two measurements as set out below. It should be noted that there is an additional rearward movement of the body region 4 allowed by the tension spring 9 which itself creates an additional translation reading. This additional translation length is measured as displacement along the force scale 12 and should be subtracted from the overall body translation length reading on the translation scale 14. For example, the application of a 101b anterior load to the ACL 24 may give a force reading on the force scale 12 of 5 mm. The total translation measured on the translation scale may be 8 mm, therefore, the true translation of the ACL 24 would be 8 mm–5 mm=3 mm of translation.

In order to use the equipment effectively, it is important to assess an average translation at a given or fixed force for a normal, healthy ACL 24. This can be done during routine arthroscopies. Once an average value of the tension of normal healthy ACLs 24 has been obtained, the surgeon aims to reproduce this by tensioning the distal end of a graft ACL 24 and measuring the translation of his ACL 24. This should be repeated until the reference translation is achieved in the joint, at which time the ACL 24 can be locked in place either immediately, or following cycling of the joint and re-checking the tension in case any stretch of tissues or proximal fixation slippage has occurred. It should be noted that it is not necessary to apply excessive force to the normal or graft ACL 24 to achieve accurate results. Applying the same force time after time is the key to reproducibility.

It should be further noted that although the above example refers to ACL 24 fixation, this invention is not limited to this application and it will be clear to the skilled technician that the device has numerous applications in connection with the replacement of any ligaments in the body.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extend to any novel one, or any novel combination, of the features disclosed in this specification (including any accompanying claims, abstract and drawings), or to any novel one, or any novel combination, of the steps of any method or process so disclosed.

What is claimed is:

1. A tension measuring device suitable for measuring the tension of soft tissue attached to bone, the device comprising a body region, force applying means extending from said body and operable to apply a translational force to soft tissue attached to bone, and abutment means extending from said body and operable to abut, in use, a bone to which the soft tissue is attached, the abutment means being responsive to the application of translational movement to the force applying means to thereby measure the applied translational movement and the force applying means being responsive to the tension in the soft tissue to transfer said applied translational movement to the soft tissue below a predetermined soft-tissue tension and to extend above the said predetermined tension to prevent further translation of the soft tissue.

2. A tension measuring device according to claim 1, wherein the extension of the force applying means is measured by measuring means comprising an associated translation scale.

3. A tension measuring device according to claim 1, wherein the force applying means is resiliently longitudinally deformable.

4. A tension measuring device according to claim 1, wherein the abutment means is resiliently longitudinally deformable.

5. A tension measuring device according to claim 1, wherein the abutment means distal end is biased towards the bone in use to remain in contact therewith during the application of translational movement away from the bone.

6. A tension measuring device according to claim 1, wherein the force applying means is under a fixed tension with respect to elongation thereof.

7. A tension measuring device according to claim 1, wherein the device measures the tension in the soft tissue by determining the extent of the translational movement of the soft issue in response to the force applying means.

8. A tension measuring device according to claim 1, wherein the force applying means and the abutment means extend outwardly in the same direction from the body region.

9. A tension measuring device according to claim 1, wherein the abutment means comprises an elongate shaft and resilient means which urges the elongate shaft into abutment with the bone.

10. A tension measuring device according to claim 1, wherein the abutment means comprises locking means to lock the abutment means in a retracted position.

11. A tension measuring device according to claim 10, wherein the locking means is releasable thereby urging the biased abutment means outwards towards the bone.

12. A tension measuring device according to claim 1, wherein the abutment means comprises translation measuring means comprising a translation scale on which translation of the body region with respect to the bone may be measured via the extension of the abutment means.

13. A tension measuring device according to claim 1, wherein the force applying means is a pulling means which is optionally placed in direct contact with the soft tissue to which the translation force is to be applied.

14. A tension measuring device according to claim 13, wherein the pulling means is adapted at its distal end to abut at least part of the rearwardly facing side of the soft tissue with respect to the body of the device.

15. A tension measuring device according to claim 13, wherein the pulling means comprises resilient means which is arranged to apply a pre-determined force to the soft tissue resulting from the translational movement applied to the tissue by the user.

16. A tension measuring device according to claim 1, wherein means are provided to determine the translational movement in the tissue by subtracting the elongation of the force applying means from the applied translational movement.

17. A method of measuring the tension of soft tissue attached to at least one bone comprising applying a translational movement under a pre-determined force to the tissue using a force applying means on a device according to claim 1 to thereby cause a measurable translational movement of the tissue with respect to the said at least one bone.

18. A method according to claim 17, wherein the method comprises one or more of the steps of:
    (i) introducing the force applying means to the soft tissue;
    (ii) urging the abutment means against at least one bone in contact with the said soft tissue; and
    (iii) applying the force to the soft tissue such that the translational movement is in the direction required.

19. A method according to claim 17, wherein the translational movement applied and the elongation of the force applying means is measured and, it is from these that the tension of the soft tissue is determined.

20. A method according to claim 17, wherein the translation force is applied to the soft tissue via the force applying means by moving the body of the device away from the soft tissue whilst the abutment means remains in contact with the bone.

* * * * *